United States Patent [19]
Oishi et al.

[11] Patent Number: 5,292,818
[45] Date of Patent: Mar. 8, 1994

[54] METHOD FOR PRODUCING A CARRIER FOR CATION EXCHANGE LIQUID CHROMATOGRAPHY AND A METHOD FOR DETERMINING GLYCOSYLATED HEMOGLOBINS USING THE CARRIER

[75] Inventors: Kazuyuki Oishi, Kyoto; Kazutoshi Yamazaki; Toshiki Kawabe, both of Ohtsu; Masahiro Takechi, Takatsuki; Makoto Takahara, Mishima, all of Japan

[73] Assignee: Sekisui Kagaku Kogyo Kabushiki Kaisha, Osaka, Japan

[21] Appl. No.: 915,685
[22] PCT Filed: Nov. 21, 1990
[86] PCT No.: PCT/JP90/01522
§ 371 Date: Jul. 20, 1992
§ 102(e) Date: Jul. 20, 1992
[87] PCT Pub. No.: WO92/09889
PCT Pub. Date: Nov. 6, 1992

[51] Int. Cl.$^5$ .................. C08F 265/04; G01N 33/72
[52] U.S. Cl. .................. 525/301; 525/302; 525/304; 525/305; 525/308; 436/67
[58] Field of Search .......... 525/301, 302, 304, 305, 525/308

[56] References Cited

U.S. PATENT DOCUMENTS

| | | | |
|---|---|---|---|
| 2,858,281 | 10/1958 | Bauman et al. | 525/301 |
| 3,489,699 | 1/1970 | Battaerd et al. | 525/287 |
| 3,565,833 | 2/1971 | Battaerd | 525/301 |
| 4,687,814 | 8/1987 | Chaumont et al. | 525/301 |

FOREIGN PATENT DOCUMENTS

| | | |
|---|---|---|
| 56-151712 | 11/1981 | Japan. |
| 58-221164 | 12/1983 | Japan. |
| 59-18705 | 1/1984 | Japan. |
| 62-63856 | 3/1987 | Japan. |
| 63-75558 | 4/1988 | Japan. |
| 63-79064 | 4/1988 | Japan. |
| 2-85758 | 3/1990 | Japan. |

*Primary Examiner*—Vasu S. Jagannathan
*Attorney, Agent, or Firm*—Renner, Otto, Boisselle & Sklar

[57] ABSTRACT

According to the present invention, a production method of a carrier appropriate for cation exchange liquid chromatography and a method for determining glycosylated hemoglobins using the carrier obtained by the production method are provided.

The production method of the carrier comprises the steps of providing hydrophobic particles to which a polymerization initiator is adhered; and adding a polymerizable monomer having a carboxyl group to an aqueous dispersion in which the hydrophobic cross-linked polymer particles are dispersed and polymerizing the monomer on surfaces of the hydrophobic cross-linked polymer particles, thereby obtaining polymer particles the surfaces of which are coated with polymer layers having carboxyl groups.

19 Claims, 7 Drawing Sheets

METHOD FOR PRODUCING A CARRIER FOR CATION EXCHANGE LIQUID CHROMATOGRAPHY AND A METHOD FOR DETERMINING GLYCOSYLATED HEMOGLOBINS USING THE CARRIER

TECHNICAL FIELD

The present invention relates to a production method of a carrier appropriate for cation exchange liquid chromatography and a method for determining glycosylated hemoglobins utilizing the carrier obtained by the production method.

BACKGROUND ART

A liquid chromatography is used for a separation or a detection of various materials, and especially for a separation or a detection of a hydrophilic material, for example, for a separation of protein from a biological sample, an ion exchange chromatography is used. Ion exchange chromatography is a method in which a carrier having an ion exchange group is utilized for separating materials depending upon a difference in the strength of an ionic bond of the material to be separated to the carrier. A weak cation exchange chromatography utilizing a carrier having a carboxyl group as the ion exchange group is effective for an analysis of protein or peptide.

For example, glycosylated hemoglobins in blood are measured with ion exchange chromatography utilizing such a carrier.

The glycosylated hemoglobins are formed by a nonenzymatical reaction of hemoglobin in an erythrocyte with glucose in the blood. Since a measurement of glycosylated hemoglobins reveals an average concentration of glucose in the blood, the measurement of the glycosylated hemoglobins is widely used for the diagnosis of diabetes. The glycosylated hemoglobins are now determined by a high performance liquid chromatography (hereinafter referred to as the "HPLC") mainly utilizing the above-mentioned carrier. The HPLC provides rapid measurement as compared with conventional column chromatography, electrophoresis, colorimetric analysis and the like.

An organic polymer carrier or an inorganic carrier is generally used as a carrier for weak cation exchange chromatography. A carrier gel of organic polymers used most frequently is a carrier in which carboxyl groups are introduced on a surface of a particle of a styrene-divinylbenzene crosslinked copolymer. Such a carrier is obtained by introducing carboxyl groups to a particle of a styrene-divinylbenzene crosslinked copolymer by a chemical reaction. For example, alkyl halide is introduced to a benzene ring of styrene in the copolymer by treating the particle of the copolymer with chloromethyl ether and the like, and the resultant material is hydrolyzed and oxidized, thereby introducing the carboxyl groups.

An example of the organic polymer carrier, besides the above-mentioned gel, includes particles of a crosslinked copolymer of styrene, divinylbenzene and a monomer having a carboxyl group. Moreover, Japanese Laid-Open Patent Publication No. 58-221164 discloses a carrier made of a copolymer of an acrylate or a methacrylate such as tetramethylolmethane triacrylate and acrylic acid or methacrylic acid. Such a carrier is generally prepared in a method disclosed in the foregoing Japanese Laid-Open Patent Publication No. 58-221164: for example, the crosslinked copolymer particles are prepared by adding a polymerization initiator to a mixture of a crosslinkable monomer and a monomer having a carboxyl group for a suspension polymerization. Alternatively, particles obtained by copolymerizing styrene, divinylbenzene and a monomer having a functional group which can be converted into a carboxyl group by a hydrolytic reaction (hereinafter referred to as the "hydrolyzable group") and then converting the functional group into a carboxyl group by a hydrolytic reaction can be used. It is necessary to increase the degree of the crosslink in order to improve the pressure resistance of such a carrier. However, when the degree of the crosslink is increased, the hydrophobicity of the gel is also increased since a crosslinked portion is hydrophobic, resulting in a nonspecific adsorption of protein. Therefore, the amount of a crosslinking agent to be used is limited, and it is difficult to obtain a satisfactory pressure resistance. Moreover, since the carrier obtained in the above-mentioned manner contains carboxyl groups in the entire copolymer particle, the carrier is likely to swell or shrink in an aqueous solvent. This is another reason for its insufficient pressure resistance.

The above-mentioned carrier used in determining glycosylated hemoglobins in high performance liquid chromatography shows the following defects:

Generally, glycosylated hemoglobins are determined by utilizing an eluent with a low eluting ability (hereinafter called "first eluent") and an eluent with a high eluting ability (hereinafter called "second eluent") in steps or in a linear gradient method. The first eluent increases a number of free carboxyl groups in the carrier particles. Thus, hemoglobin in a sample except for glycosylated hemoglobins is retained by the carrier, thereby separating and eluting the glycosylated hemoglobins. Since the second eluent has a large ionic strength, the free carboxyl groups become salts. Therefore, the retained hemoglobin except for the glycosylated hemoglobins is rapidly eluted.

However, in the above-mentioned carrier, especially in the carrier prepared by using a hydrophobic monomer and a hydrophilic monomer such as a monomer having a carboxyl group or a latent carboxyl group, ion exchange groups derived mainly from the hydrophilic monomer are present throughout the carrier particle. When such a carrier comes in contact with the second eluent, the carrier swells, thereby increasing pressure in the column. It is necessary to return the carboxyl groups to be free by letting the first eluent flow after measuring one sample in order to measure another sample. At this point, in order to return the ion exchange groups existing in the carrier to be sufficiently free, it is necessary to let a considerable amount of the first eluent flow. Therefore, a longer time is required for the measurement. Glycosylated hemoglobins can now be measured relatively rapidly by the HPLC utilizing a carrier gel of polymer. However, when attempting to increase the measuring rate, the separating ability is degraded, because the ion exchange groups in the carrier can not be sufficiently exchanged or the carrier swells. In order to achieve an accurate separation, it is necessary to decrease the eluting rate.

On the other hand, as an inorganic carrier used for the separation of protein from an ordinary biological sample, Japanese Laid-Open Patent Publication No. 63-75558 discloses a silica carrier in which carboxyl groups are chemically bonded to a surface of a porous silica gel. This carrier has a satisfactory pressure resistance and separating ability, and can provide a relatively rapid treatment. However, this gel has a characteristic of adsorbing a material having basic groups such as protein due to an effect of residual silanol groups on the surface thereof. Moreover, since silica gel is dissolved in an acid and an alkali, pH of the eluent is limited from 3 to 8.

Moreover, a so called seed polymerization is disclosed in Japanese Laid-Open Patent Publication Nos. 56-151712, 59-18705, 62-63856 and 63-79064 as a method for obtaining a carrier which can be used as a carrier in weak cation exchange chromatography and has a relatively satisfactory pressure resistance. This method is such that crosslinked polymer particles are impregnated with a polymerization initiator and a monomer, and the impregnated particles are suspension-polymerized in order to obtain two-layered particles. When a monomer having a carboxyl group is used as the monomer for impregnating the crosslinked polymer particles in this method, a carrier for weak cation exchange chromatography can be obtained. A similar carrier for weak cation exchange chromatography as the above can be obtained by impregnating the particles with a monomer having a functional group which can be converted into a hydrolyzable group, polymerizing the said monomer, and then hydrolyzing the hydrolyzable groups owned by the particles. However, since the thus obtained particles have carboxyl groups therein, the particles are likely to swell or shrink in an aqueous solvent due to the foregoing reasons, resulting in an insufficient pressure resistance. Moreover, there are defects in that the separating ability of liquid chromatography is degraded or it takes a longer time for the separation when such a carrier is used.

DISCLOSURE OF INVENTION

A first production method of a carrier for cation exchange liquid chromatography according to the present invention is to solve the various problems described in the above-mentioned paragraphs on the background art and comprises the steps of:

providing an aqueous dispersion in which hydrophobic crosslinked polymer particles to which a polymerization initiator is adhered are dispersed; and adding a polymerizable monomer having a carboxyl group to the aqueous dispersion and polymerizing the monomer on the surface of the hydrophobic crosslinked polymer particle, thereby forming a polymer layer having carboxyl groups on the surface of the hydrophobic crosslinked polymer particle to obtain a coated polymer particle.

In a preferred embodiment, the hydrophobic crosslinked polymer is obtained by homopolymerizing or copolymerizing at least one kind of a hydrophobic crosslinkable monomer, or copolymerizing at least one kind of a hydrophobic crosslinkable monomer and at least one kind of a hydrophobic noncrosslinkable monomer.

In a preferred embodiment, the hydrophobic crosslinkable monomer is at least one selected from the group consisting of di(metha)acrylates, poly(metha)acrylates of polyhydric alcohols and aromatic compounds having at least two vinyl groups.

In a preferred embodiment, the hydrophobic noncrosslinkable monomer is at least one selected from the group consisting of (metha)acrylates, vinyl acetate and styrene type monomers.

In a preferred embodiment, the polymerizable monomer having a carboxyl group is at least one selected from the group consisting of acrylic acid, methacrylic acid, maleic acid, fumaric acid and crotonic acid.

In a preferred embodiment, the coated polymer particle does not substantially have any pores or is a porous particle with pores having an average radius of 10,000 angstroms or less.

In a preferred embodiment the aqueous dispersion in which the hydrophobic crosslinked polymer to which the polymerization initiator is adhered is dispersed is obtained by reacting monomers having a hydrophobic crosslinkable monomer in the presence of the polymerization initiator.

A second production method of a carrier for a cation exchange liquid chromatography according to the present invention comprises steps of providing an aqueous dispersion in which hydrophobic crosslinked polymer particles without any hydrolyzable groups to which a polymerization initiator is adhered are dispersed, adding a monomer having a functional group which can be converted into a carboxyl group by a hydrolytic reaction to the aqueous dispersion to be dissolved therein and polymerizing the monomer on the surface the polymer particle, thereby forming a layer of the polymer having the functional groups on the surface of the hydrophobic crosslinkable polymer particle, and hydrolyzing the functional groups to obtain a coated polymer particle having carboxyl groups on the surfaces thereof.

In a preferred embodiment in the second method, the hydrophobic crosslinked polymer is obtained by homopolymerizing or copolymerizing at least one kind of a hydrophobic crosslinkable monomer, or copolymerizing at least one kind of a hydrophobic crosslinkable monomer and at least one kind of a hydrophobic noncrosslinkable monomer.

In a preferred embodiment in the second method, the hydrophobic crosslinkable monomer is an aromatic compound having at least two vinyl groups.

In a preferred embodiment in the second method, the hydrophobic noncrosslinkable monomer is a styrene type monomer.

In a preferred embodiment in the second method, the monomer having the functional group which can be converted into a carboxyl group by a hydrolytic reaction is selected from the group consisting of alkyl (metha)acrylates, (metha)acrylamide and (metha)acrylonitrile.

In a preferred embodiment in the second method, the coated polymer does not substantially have any pores or is a porous particle with pores having an average radius of 10,000 angstroms or less.

In a preferred embodiment in the second method, the aqueous dispersion in which the hydrophobic crosslinked polymer to which the polymerization initiator is adhered is dispersed is obtained by reacting monomers including the hydrophobic crosslinkable monomer without a hydrolyzable group in the presence of polymerization initiator.

In a method for determining glycosylated hemoglobins in a sample in liquid chromatography in accordance with the present invention, a carrier used in liquid chromatography is obtained in the first or the second production method.

Therefore, the present invention can achieve the following objectives:

(1) providing a method for producing a carrier for cation exchange liquid chromatography appropriate for a separation of hydrophilic materials such as protein which has a high pressure resistance, hardly swells or shrinks, and hardly adsorbs protein and the like nonspecifically;

(2) providing a method for separating and determining glycosylated hemoglobins by the HPLC accurately in a short period of time; and (3) providing a method for effectively determining glycosylated hemoglobins by the HPLC using a carrier which does not increase column pressure while operating the column, which is rapidly equilibrated with an eluent and which does not nonspecifically adsorb protein and the like.

BEST MODE FOR CARRYING OUT THE INVENTION

Figure 1:
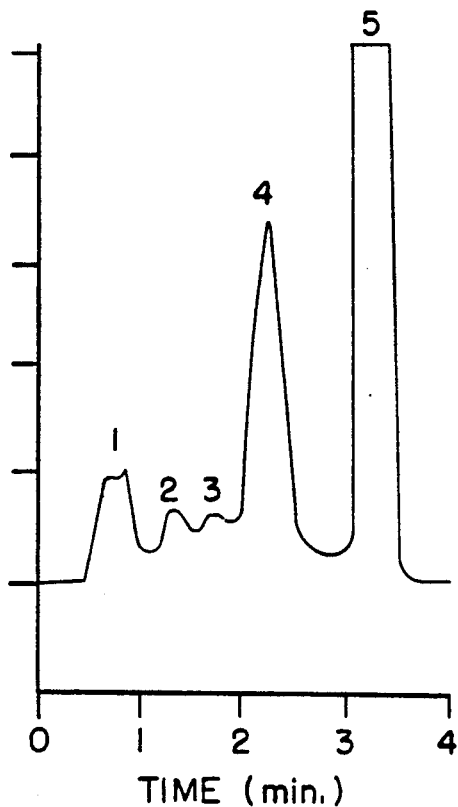
FIGS. 1, 3, 5, 8, 10 and 12 show chromatograms obtained in analyses of glycosylated hemoglobins in blood utilizing columns packed with carriers obtained in Example 1, Example 2, Comparative Example 1, Example 5, Example 6 and Comparative Example 5, respectively.

As a material of hydrophobic crosslinked polymer particles used in a first and a second production methods of the present invention, a hydrophobic crosslinked polymer obtained by homopolymerizing or copolymerizing at least one kind of a hydrophobic crosslinkable monomer, or a copolymer of at least one kind of a hydrophobic crosslinkable monomer and at least one kind of a hydrophobic noncrosslinkable monomer can be used.

Examples of the hydrophobic crosslinkable monomer used in the first production method include di(metha)acrylates such as ethyleneglycol di(metha)acrylate, polyethyleneglycol di(metha)acrylate, propyleneglycol di(metha)acrylate and polypropyleneglycol di(metha)acrylate; poly(metha)acrylates of polyhydric alcohols such as tetramethylolmethane tri(metha)acrylate and tetramethylolmethane tetra(metha)acrylate; and aromatic compounds having two or more vinyl groups such as divinylbenzene, divinyltoluene, divinylxylene and divinylnaphtalene. As the hydrophobic noncrosslinkable monomer used in the first production method, any hydrophobic noncrosslinkable polymerizable monomer can be used. For example, (metha)acrylates such as methyl (metha)acrylate, ethyl (metha)acrylate, propyl (metha)acrylate, isopropyl (metha)acrylate, butyl (metha)acrylate and t-butyl (metha)acrylate; vinyl acetate; and styrene type monomers such as styrene and methylstyrene can be used. When a mixture of the crosslinkable and noncrosslinkable monomers is used, 10 parts by weight or more, preferably 20 parts by weight or more, of the crosslinkable monomer is used for every 100 parts by weight of the entire monomers.

As a monomer used to form a polymer layer having carboxyl groups on a surface of the hydrophobic crosslinked polymer particle in the first production method of the present invention, a monomer having a carboxyl group is used. For example, acrylic acid, methacrylic acid, maleic acid, fumaric acid, crotonic acid or other polymerizable monomers having a carboxyl group is used.

Two or more kinds of the polymerizable monomers having a carboxyl group are used in a mixture, if necessary. A used amount of such a monomer varies depending upon the kind of the monomer, but a rate of 5 to 80 parts by weight for every 100 parts by weight of the hydrophobic crosslinked polymer is appropriate.

As a material of the hydrophobic crosslinked polymer particles having no hydrolyzable groups used in the second production method (the hydrolytic method) of the present invention, a (co)polymer obtained by (co)polymerizing hydrophobic crosslinkable monomers or a copolymer of a hydrophobic crosslinkable monomer and a hydrophobic noncrosslinkable monomer is used. The hydrophobic crosslinkable monomer and the hydrophobic noncrosslinkable monomer can be used alone, respectively, or in combination with two kinds or more can be used. As the hydrophobic crosslinkable monomer, for example, aromatic compounds having two or more vinyl groups such as divinylbenzene, divinyltoluene, divinylxylene, and divinylnaphtalene are used. As the hydrophobic noncrosslinkable monomer, for example, styrene type monomers such as styrene and methylstyrene are used. When a mixture of the crosslinkable and noncrosslinkable monomers is used, 10 parts by weight or more, preferably 20 parts by weight or more, of the crosslinkable monomer is used for every 100 parts by weight of the entire monomers.

The monomer used for forming a polymer for coating the hydrophobic crosslinked polymer particles in the second production method of the present invention is a monomer having a hydrolyzable group. Examples of such a monomer include alkyl esters of acrylic acid or methacrylic acid (hereinafter referred to as "(metha)acrylic acid") such as methyl acrylate and methyl methacrylate; and (metha)acrylamide and (metha)acrylonitrile. A mixture of two or more kinds of the monomers having hydrolyzable groups can be used, if necessary. A used amount of the monomer having a hydrolyzable group varies depending upon the kind of the monomer, but a rate of 5 to 80 parts by weight for every 100 parts by weight of the hydrophobic crosslinked polymer is preferable.

In order to prepare a carrier for liquid chromatography in the first or the second production method of the present invention, firstly, the hydrophobic crosslinked polymer particles are prepared in the following manner. The hydrophobic crosslinked polymer particles can be prepared in any of the known aqueous suspension polymerizations. For example, the hydrophobic crosslinkable monomer is mixed with a polymerization initiator and a hydrophobic noncrosslinkable monomer, if necessary. They are dissolved in a diluent, if necessary. When the monomer is dissolved in the diluent, an organic solvent, the diluent, is dispersed in the obtained polymer particles. Therefore, porous spherical particles are obtained by removing the organic solvent after the polymerization. The size of a pore of the porous polymer can be optionally changed by using, as the diluent, various organic solvents with compatibilities different from that of the mixture of the hydrophobic monomer. Since the hydrophobic crosslinked polymer particle need not necessarily be porous, it is not always necessary to add the diluent. When the diluent is used, 200 parts by weight or less is ordinarily used for every 100 parts by weight of the mixture of the monomers. The diluted monomer, or the monomer and the polymerization initiator are added to an aqueous solution with a suspension stabilizer such as polyvinyl alcohol or calcium phosphate dissolved therein. After supplying nitrogen to displace the air in the reaction system, the mixture is heated to a temperature of 40° C. to 100° C. with stirring for a suspension polymerization.

The polymerization initiator used at this point and a polymerization initiator for adhering to the obtained hydrophobic crosslinked polymer particles (described below) are catalyst generating radicals, and are not especially limited as long as they are hydrophobic. Any of the known radical generating catalyst such as organic peroxides such as benzoyl peroxide, acetyl peroxide and cumene peroxide; and azo compounds such as azobisisobutyronitrile and azobisisobutyroamide can be used.

As the diluent, any of the organic solvents which can dissolve the monomer but not dissolve the polymer thereof can be used. The examples include aromatic hydrocarbons such as toluene, xylene, diethylbenzene and dodecylbenzene; saturated hydrocarbons such as hexane, heptane, octane and decane; and alcohols such as isoamyl alcohol, hexyl alcohol and octyl alcohol.

Next, a polymerization initiator is adhered to the thus obtained hydrophobic crosslinked polymer particles. "The polymerization initiator is 'adhered' to the hydrophobic crosslinked polymer particles" herein means that the polymerization initiator is adhered to the surfaces of the hydrophobic crosslinked polymer particles or that the polymerization initiator is adhered to the surfaces of the particles and allowed to impregnate inner parts of the particles near the surfaces. In order to adhere the polymerization initiator, the polymerization initiator is dissolved in a solvent with a low boiling point and a high affinity with the hydrophobic crosslinked polymer, and the hydrophobic crosslinked polymer particles are immersed therein. Thus, polymerization initiator is impregnated into the particles. The resultant is heated at a temperature below a decomposition point of the polymerization initiator, if necessary, to remove the solvent, thereby obtaining the hydrophobic crosslinked polymer particles including the polymerization initiator. In the first production method of the present invention, the particles to which the polymerization initiator is adhered are dispersed in an aqueous dispersion medium with the polymerizable monomer having a carboxyl group dissolved therein, or the monomer is added to be dissolved in an aqueous medium with the particles dispersed therein. Next, in an atmosphere of nitrogen the resultant is heated with stirring and allowed to polymerize. A dispersion stabilizer such as carboxymethyl cellulose or polyvinyl alcohol may be added to the aqueous dispersion medium in order to stabilize the dispersibility of the hydrophobic crosslinked polymer. The temperature and the time required for the polymerization depends upon the kind of the monomer to be reacted and the kind of the polymerization initiator, and are generally 40° C. to 100° C. and about 0.5 to 40 hours, respectively.

Besides the above described method in which the crosslinked polymer particles to which the polymerization initiator is adhered are provided to polymerize with the monomer having a carboxyl group, the above-mentioned two-layered polymer particles can be prepared by a continuous method in which a polymerizable monomer having a carboxyl group is allowed to react subsequently after the preparation of the hydrophobic crosslinked polymer particles. In this method, a polymerizing reaction for preparing the crosslinked polymer particles is allowed to start first. When the polymerization is proceeded to some degree and the unreacted polymerization initiator still remains, the monomer having a carboxyl group is added to the reaction system. Since the polymerization initiator exists within an organic phase in the system and within the produced hydrophobic crosslinked polymer particles under such a condition, the polymerization of the monomer is successively caused and a polymer layer having carboxyl groups is formed so as to coat surfaces of the hydrophobic crosslinked polymer particles.

The thus obtained polymer particles are sufficiently washed with hot water or an organic solvent to remove the suspension stabilizer, the solvent and the residual monomer included in or adhered to the particles. The resultant particles are classified, if necessary, thereby obtaining a carrier for the cation exchange liquid chromatography.

In the second production method of the present invention, the particles to which the polymerization initiator is adhered are dispersed in a dispersion medium with a monomer having a hydrolyzable group dissolved therein, or a monomer having a hydrolyzable group is added to a dispersion medium with the particles dispersed therein, dissolved therein, and heated with stirring in an atmosphere of nitrogen for a polymerization. By this polymerization, the monomer having a hydrolyzable group is polymerized in the surface of the hydrophobic crosslinked polymer particle, thereby coating the particle. As the dispersion medium, water or an organic solvent which can dissolve the monomer having a hydrolyzable group, or a mixture thereof is used. A dispersion stabilizer such as carboxymethyl cellulose and polyvinyl alcohol may be used to stabilize the dispersibility of the hydrophobic crosslinked polymer in the dispersion medium. The temperature and the time required for the polymerization depends upon the kind of the monomer having a hydrolyzable group to be reacted and the kind of the polymerization initiator, and are generally 40° C. to 100° C. and about 0.5 to 40 hours, respectively. In this way, the two-layered polymer particles are prepared.

Besides the foregoing method in which the hydrophobic crosslinked polymer particles to which the polymerization initiator is adhered are provided to polymerize with the monomer having a hydrolyzable group, the two-layered polymer particles can be prepared in a continuous method in which the monomer having a hydrolyzable group is allowed to react subsequently after the preparation of the hydrophobic crosslinked polymer particles. In this method, the polymerization reaction for preparing the hydrophobic crosslinked polymer particles is started first. When the polymerization is proceeded to some degree and the unreacted monomer still remains, the monomer having a hydrolyzable group is added to the reaction system. Since the polymerization initiator exists within an organic phase in the system and within the produced hydrophobic crosslinked polymer particles under such a condition, the polymerization of the monomer having a hydrolyzable group is successively caused and a polymer layer having the hydrolyzable groups is formed so as to coat the surfaces of the hydrophobic crosslinked polymer particles.

The thus obtained polymer particles are sufficiently washed with hot water or an organic solvent to remove the suspension stabilizer, the solvent and the residual monomer included in or adhered to the particles.

The thus obtained polymer particles are hydrolyzed by treating with an acid catalyst or an alkaline catalyst, for example, at a temperature of 40° C. to 100° C. for 0.5 to 50 hours, thereby hydrolyzing hydrolyzable functional groups existing in the coated layer on the surface of the particle to convert into carboxyl groups. For example, when methyl acrylate is used as the monomer having a hydrolyzable group, a $COOCH_3$ group on the surface of the particle converts into a carboxyl group by reacting the polymer particle in a 15 to 25% by weight methanol solution of sodium hydroxide at a temperature of 60° C. to 80° C. for 4 to 20 hours.

After the hydrolytic reaction, the polymer particles are recovered by filtration, washed with water and dried. The particles are classified, if necessary, to obtain a carrier for the weak cation exchange chromatography.

An average particle diameter of the carrier obtained by the present invention varies depending upon the stirring rate at the preparation of the hydrophobic crosslinked polymer, the kind and an amount of the dispersion solvent and the kind of the hydrophobic monomer, and is generally in the range of 1 to 1000 $\mu$m, preferably in the range of 2 to 100 $\mu$m. As described above, the carrier of the present invention is not necessarily porous. However, when it is porous, an average radius of a pore is 10,000 angstroms or less, preferably 5,000 angstroms or less.

The carrier obtained in the production method of the present invention is a two-layered polymer particle which has a core of a hydrophobic crosslinked polymer, the surface of which is coated with a polymer having carboxyl groups. An average thickness of the coated layer of the polymer having the carboxyl groups is preferably 10 to 300 angstroms. The thickness of the coated layer is measured in accordance with "a method for measuring the average thickness of the coated layer" described in the following examples. When the average thickness is less than 10 angstroms, the coating is incomplete, and the surfaces of the hydrophobic crosslinked polymer particles tend to be exposed. When there is such an exposed surface, a material to be separated (for example, protein) may be nonspecifically adsorbed on the carrier. When the average thickness exceeds 300 angstroms, the coated layer itself is largely swollen or shrunk, thereby degrading a separating ability of the carrier and increasing pressure during the analysis. Moreover, an equilibrium with the eluent requires a longer time, resulting in a longer analysis time or a degraded separating ability.

Since the carrier particles obtained in the production method of the present invention contain a polymer with a high crosslinking degree in its core, the mechanical strength thereof is extremely large and the pressure resistance thereof is satisfactory. Moreover, since the core of the carrier does not have a hydrophilic group, the degree of swelling and shrinking is extremely low. Since the surface thereof is coated with a hydrophilic polymer having carboxyl groups, it does not nonspecifically adsorb protein and the like. A degree of hydrophilicity of the particle surface and an ion exchanging ability can be controlled by selecting an appropriate monomer having a carboxyl group, therefore, a desired carrier for cation exchange chromatography suitable for the hydrophilic material to be analyzed or to be separated can be obtained. The carrier can be used in a wide range of pH. Due to the above-mentioned large pressure resistance and a low degree of swelling and shrinking, the particle diameter can be minimized, resulting in an accurate separation. Since it can be used under high pressure, the analysis can be performed rapidly.

By using the obtained carrier, glycosylated hemoglobins in blood are measured. In order to measure glycosylated hemoglobins according to the present invention, a sample blood is first hemolyzed, if necessary. The sample blood is then applied on a column packed with the carrier, thereby determining glycosylated hemoglobins in an ordinary manner of liquid chromatography. The glycosylated hemoglobins, and other hemoglobins are separated to be successively eluted by using a selected appropriate buffer.

The carrier used in the present invention is made of a two-layered polymer particle with a core of a hydrophobic crosslinked polymer, the surface of which is coated with a polymer having carboxyl groups. The carrier for liquid chromatography with an extremely large mechanical strength and a satisfactory pressure resistance can be obtained by using a polymer with a large degree of crosslinking as the core. Since the core of the carrier does not have a hydrophilic group, a degree of swelling and shrinking is extremely low. Therefore, in determining glycosylated hemoglobins, an increase of pressure at the time of letting the second eluent flow is extremely small. Only the surface is covered with the polymer layer having carboxyl groups, therefore, an ion exchanging ability of the carrier is high and the equilibrium of the carboxyl groups is performed very rapidly. As a result, the separating ability for the glycosylated hemoglobins is excellent, and a measurement in a short period of time can be realized. Moreover, a nonspecific adsorption of protein can not be found.

EXAMPLES

The present invention will be further described by following examples.

Methods for measuring physical properties and evaluating abilities of carriers obtained in the following examples and comparative examples are as follows:

A Method for Measuring an Average Thickness of a Coated Layer

Coated polymer particles used for the carrier were embedded in an epoxy resin, and then a slice with a thickness of about 900 angstroms was obtained by using a microtome ULTRACUTE produced by Reichert-Jung Co. The slice was labeled by using a silver nitrate solution (for a volumetric analysis, produced by Wako Pure Chemical Industries, Ltd.), observed and photographed by using a transmission electron microscope JEM 100S produced by Nihon Denshi Kabushiki Kaisha. Thus a distributing condition of carboxyl groups was evaluated, and an average thickness of the coated layer was measured.

A Method for Evaluating a Carrier

The obtained carrier was packed in a stainless column with an inner diameter of 6 mm and a length of 75 mm, and the pressure resistance and the swelling property with water were checked. The pressure resistance was measured on the basis of the relationship between the flow rate and the pressure loss when pure water was allowed to flow through the column at different rates.

The swelling property was measured from a change of column pressure when liquids with different ionic strength were allowed to flow.

Carboxyl groups on a surface of the gel were determined by an auto potential difference titrating device AT-310 produced by Kyoto Denshi Kogyo Kabushiki Kaisha.

Then, a specific surface area and a distribution of pores in the carrier were measured by an auto surface area measuring device SORPTOMATIC 1800 produced by Calro Elva Co.

Moreover, a human blood analysis was performed by using an Hi-AUTO $A_{1c}$ produced by Kyoto Daiichi Kagaku Kabushiki Kaisha, and the separating ability and the like were compared with those of the prior art. The measuring method was as follows: As a human blood sample, blood was obtained from one person (a healthy person), and heparin was immediately added thereto. The blood sample was automatically diluted 290-fold with a hemolysis solution 21 L (a phosphate buffer containing a nonionic surface active agent) specified to the device and hemolyzed. As eluents, reagents specified to the device, that is, eluent A (a phosphate buffer of pH 5.9), eluent B (a phosphate buffer of pH 7.2) and eluent C (a phosphate buffer of pH 5.9) were used. Eluent A corresponds to first eluent (with a low eluting ability) described in the paragraph of the background art. In evaluating a carrier with a weak retaining ability, a best separation condition was found by using an eluent obtained by further diluting eluent A in the range of 1- to 10-fold. The separating ability was evaluated under this separation condition. Separately, protein was separated from a sample containing several kinds of proteins by using a liquid chromatography system SSLC-20 produced by Sekisui Kagaku Kogyo Kabushiki Kaisha.

EXAMPLE 1

A hundred grams of styrene (a hydrophobic non-crosslinkable monomer), 200 g of divinylbenzene (a hydrophobic crosslinkable monomer) and 1 g of benzoyl peroxide (a polymerization initiator) were dissolved in 200 g of toluene. The resultant mixture was added to 2.5 L of a 4% polyvinyl alcohol aqueous solution, and the size of particles in the obtained solution was controlled with stirring, and was heated to a temperature of 80° C. in an atmosphere of nitrogen for a suspension polymerization. After polymerizing at a temperature of 80° C. for 8 hours, the resultant product was washed with hot water and acetone successively, and dried to obtain fine hydrophobic crosslinked polymer particles.

Two hundred grams of the obtained hydrophobic crosslinked polymer particles was added to 1 L of acetone with 0.5 g of benzoyl peroxide dissolved therein, thereby adhering the polymerization initiator. Then, acetone was removed under a reduced pressure at a temperature of 20° C. The hydrophobic crosslinked polymer after the adhering treatment was suspended in 2.5 L of 1% polyvinyl alcohol aqueous solution, and 50 g of acrylic acid was added thereto with stirring, and allowed for a polymerizing reaction for 2 hours at a temperature of 80° C. in an atmosphere of nitrogen. The obtained product was washed with hot water and acetone successively, and dried to obtain 180 g of fine polymer particles. The thus obtained particles were classified by an air classifier, Turbo Classifier TC-15N produced by Nisshin Engineering Kabushiki Kaisha for recovering particles with a particle diameter of 8 to 10 μm to obtain a carrier. The carrier was then packed in a stainless column with an inner diameter of 6 mm and a length of 75 mm. Two grams of the gel (the carrier) was added to 35 mL of pure water and the resultant mixture was stirred for 5 minutes. Then the column was packed with this mixture at a constant flow rate of 2.0 mL/minute.

The pressure resistance and the swelling property were evaluated by the foregoing methods. In the evaluation of the pressure resistance, a pressure loss was in proportion to the flow rate up to 150 kg/cm². In the swelling property test, column pressure did not increase when the eluent was changed from a 40 mM phosphate buffer to a 200 mM phosphate buffer.

An ion exchanging ability of the carrier obtained by titration was 0.8 meq/g. The carrier was treated with a silver nitrate solution and the thickness of the coated layer was measured in the above-mentioned manner to obtain a thickness of about 80 angstroms. The specific surface area was 50 m²/g, and an average radius of a pore was 40 angstroms.

Human blood was analyzed by the Hi-AUTO $A_{1c}$ produced by Kyoto Daiichi Kagaku Kabushiki Kaisha. The resultant chromatogram is shown in FIG. 1. In FIG. 1, and also in the following FIGS. 3, 5, 8, 10, and 12, the peak with a reference numeral 1 shows a peak resulting from $HbA_{1a}$ and $A_{1b}$, 2 from fetal Hb(F), 3 from unstable type of $HbA_{1c}$, 4 from stable type of $HbA_{1c}$ and 5 from $HbA_0$, respectively. $HbA_{1c}$ (a total of the unstable type and the stable type) herein is calculated in the following formula:

$$HbA_{1c}(\%) = \frac{\text{Total of areas of peaks 3 and 4}}{\text{Total of areas of } Hb \text{ peaks}} \times 100$$
$$(1, 2, 3, 4 \text{ and } 5)$$

There was no change in the chromatogram and the measured value of the $HbA_{1c}$ after repeating 3000 measurements using the samples of the same lot.

Figure 2:
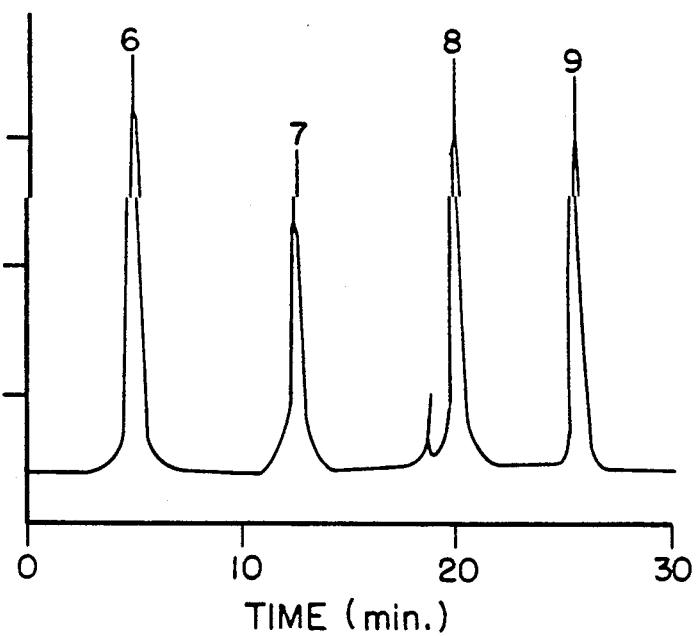
FIGS. 2, 4, 6 and 7 show chromatograms obtained in analyses of protein utilizing columns packed with carriers obtained in Example 1, Example 2, Comparative Example 1 and Comparative Example 3, respectively.

Moreover, a sample containing several kinds of proteins (produced by Sigma Co.) was analyzed by using the liquid chromatograph system SSLC-20 produced by Sekisui Kagaku Kogyo Kabushiki Kaisha. An elution was performed by using a 50 mM phosphate buffer (pH 7.0, hereinafter referred to as eluent D); and an equivalent mixture of eluent D and a 500 mM NaCl (pH 7.0) (hereinafter referred to as eluent E) in a linear gradient method from 100% of eluent D to 100% of eluent E. The resultant chromatogram is shown in FIG. 2. In FIG. 2, and also in the following FIGS. 4, 6 and 7, the peak with a reference numeral 6 shows a peak resulting from myoglobin (derived from a horse skeleton), 7 from α-chymotrypsinogen (derived from a bovine pancreas), 8 from ribonuclease A (derived from a bovine pancreas) and 9 from lysozyme (derived from a chicken egg white), respectively.

EXAMPLE 2

Hydrophobic crosslinked polymer particles were prepared in the same manner as in Example 1 by using 300 g of diethyleneglycol dimethacrylate as a hydrophobic crosslinkable monomer and 200 g of isoamyl alcohol instead of toluene as a diluent. Further, 190 g of fine polymer particles was obtained in the same manner as in Example 1 by using 50 g of methacrylic acid as the monomer having a carboxyl group. The resultant particles were classified to obtain a carrier with a particle diameter of 8 to 10 μm.

Figure 3:
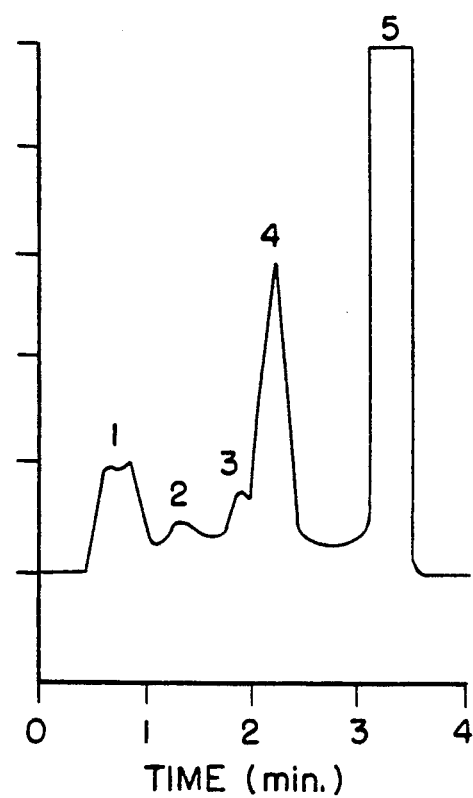
Figure 4:
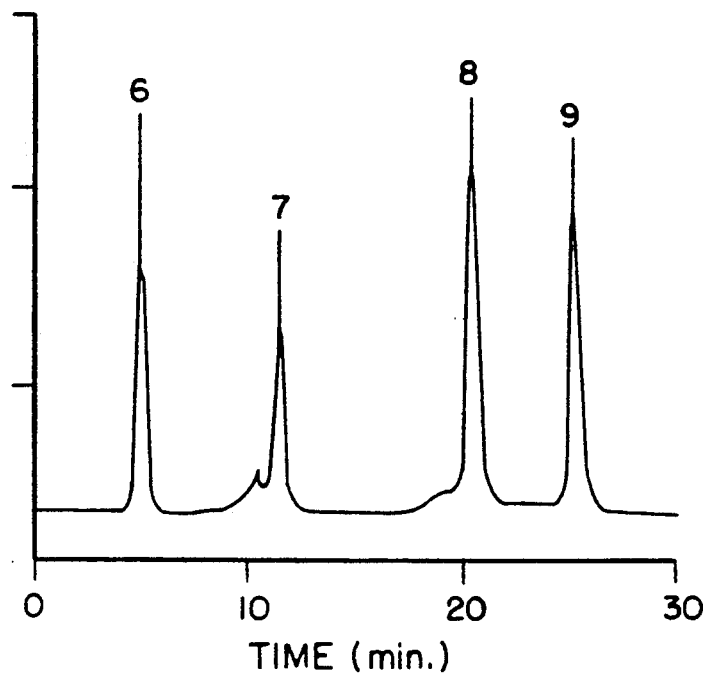

As a result of the same evaluation as in Example 1, as for the pressure resistance, the pressure loss was in proportion to the flow rate up to 150 kg/cm$^2$. In the swelling property test, the column pressure did not increase when the eluent was changed from a 40 mM phosphate buffer to a 200 mM phosphate buffer. The ion exchanging ability of the carrier measured by titration was 0.7 meq/g. The thickness of the coated layer measured after treating the carrier particles with a silver nitrate solution was about 100 angstroms. The specific surface area was 30 m$^2$/g, and the average radius of the pore was 20 angstroms. Then, human blood was analyzed by Hi-AUTO A$_{1c}$ produced by Kyoto Daiichi Kagaku Kabushiki Kaisha. The resultant chromatogram is shown in FIG. 3. The chromatogram and the measured value were the same after repeating 3000 measurements of samples of the same lot. Moreover, protein was separated by using the liquid chromatograph SSLC-20 produced by Sekisui Kagaku Kogyo Kabushiki Kaisha. The resultant chromatogram is shown in FIG. 4.

EXAMPLE 3

In this example, a continuous polymerization method in which a monomer having a carboxyl group is allowed to react subsequently after the preparation of hydrophobic crosslinked polymer particles was adopted.

One hundred grams of styrene as a hydrophobic non-crosslinkable monomer, 200 g of divinylbenzene as a hydrophobic crosslinkable monomer and 1 g of benzoyl peroxide were dissolved in 200 g of toluene. The obtained mixture was added to 2.5 L of an aqueous solution of 4% polyvinyl alcohol, stirred to disperse an organic phase uniformly, and then heated to 80° C. in an atmosphere of nitrogen for a suspension polymerization. After polymerizing at a temperature of 80° C. for 2 hours, 50 g of acrylic acid was added thereto. After polymerizing at a temperature of 80° C. for another 2 hours, the obtained product was successively washed with hot water and acetone, and dried to obtain 260 g of fine polymer particles. The obtained particles were classified, and those with a particle diameter of 8 to 10 μm were recovered to obtain a carrier. The obtained carrier was evaluated in the same manner as in Example 1.

As for the pressure resistance, the pressure loss and the flow rate were in proportion to each other up to 150 kg/cm$^2$. In the swelling property test, the column pressure did not increase when the eluent was changed from a 40 mM phosphate buffer to a 200 mM phosphate buffer. The ion exchanging ability measured by titration was 0.7 meq/g. The thickness of the coated layer was about 80 angstroms. The specific surface area was 70 m$^2$/g, and the average radius of the pore was 50 angstroms. Next, human blood was analyzed by the Hi-AUTO A$_{1c}$ produced by Kyoto Daiichi Kagaku Kabushiki Kaisha. The resultant chromatogram was the same as FIG. 1. Moreover, protein was separated by the liquid chromatograph SSLC-20 produced by Sekisui Kagaku Kogyo Kabushiki Kaisha. The resultant chromatogram was the same as FIG. 2.

EXAMPLE 4

Four hundred fifty grams of triethyleneglycol dimethacrylate (a hydrophobic crosslinkable monomer), 50 g of tetramethylolmethane triacrylate (a hydrophobic crosslinkable monomer) and 1.5 g of benzoyl peroxide (a polymerization initiator) were uniformly mixed. The resultant mixture was added to 2.5 L of an aqueous solution of 4% polyvinyl alcohol and stirred to disperse an organic phase uniformly. After supplying nitrogen to displace the air in the reaction system, the mixture was heated to a temperature of 80° C. and allowed for a suspension polymerization for 1 hour. The resultant mixture was cooled down to a temperature of 30° C. or less, and 300 g of methacrylic acid was added thereto to be dissolved. The obtained reaction mixture was heated to a temperature of 80° C. again and polymerized for 1 hour. The obtained product was successively washed with hot water and acetone and dried to obtain 450 g of fine polymer particles. The particles were classified in the same manner as in Example 1, and those with a particle diameter of 6 to 9 μm were recovered to obtain a carrier. The obtained carrier was evaluated in the same manner as in Example 1.

In the evaluation of the pressure resistance, the pressure loss was in proportion to the flow rate up to 600 kg/cm$^2$. In the swelling property test, the column pressure did not increase when the eluent was changed from a 40 mM phosphate buffer to a 200 mM phosphate buffer. The ion exchanging ability of the carrier measured by titration was 0.05 meq/g. The thickness of the coated layer measured after treating the carrier with a silver nitrate solution was about 90 angstroms. The specific surface area was 0.5 m$^2$/g, and there were no pores.

Human blood was analyzed by using Hi-AUTO A$_{1c}$ produced by Kyoto Daiichi Kagaku Kabushiki Kaisha. The resultant chromatogram was the same as FIG. 1. The chromatogram and the measured value of HbA$_{1c}$ were the same after repeating 3000 measurements.

Moreover, a separation under the same condition as the above was performed with a sample including several kinds of proteins by using the liquid chromatograph system SSLC-20 produced by Sekisui Kagaku Kogyo Kabushiki Kaisha. The resultant chromatogram was the same as FIG. 2.

COMPARATIVE EXAMPLE 1

A hundred grams of styrene, 200 g of divinylbenzene, 150 g of acrylic acid and 1 g of benzoyl peroxide were dissolved in 270 g of toluene. The resultant mixture was added to 2.5 L of an aqueous solution of 4% polyvinyl alcohol, stirred to disperse an organic phase uniformly and heated to a temperature of 80° C. for a suspension polymerization. After polymerizing for 8 hours, the obtained product was treated in the same manner as in Example 1 to obtain 420 g of fine polymer particles. The obtained particles were classified to obtain a carrier with a particle diameter of 6 to 9 μm.

Figure 5:
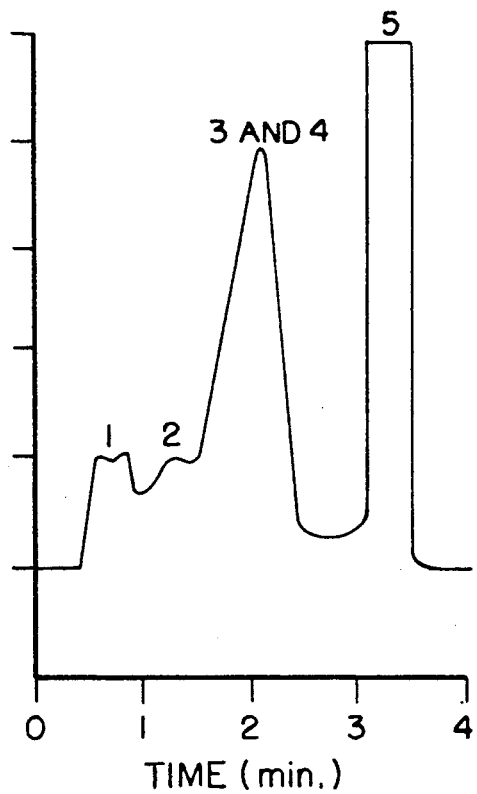
Figure 6:
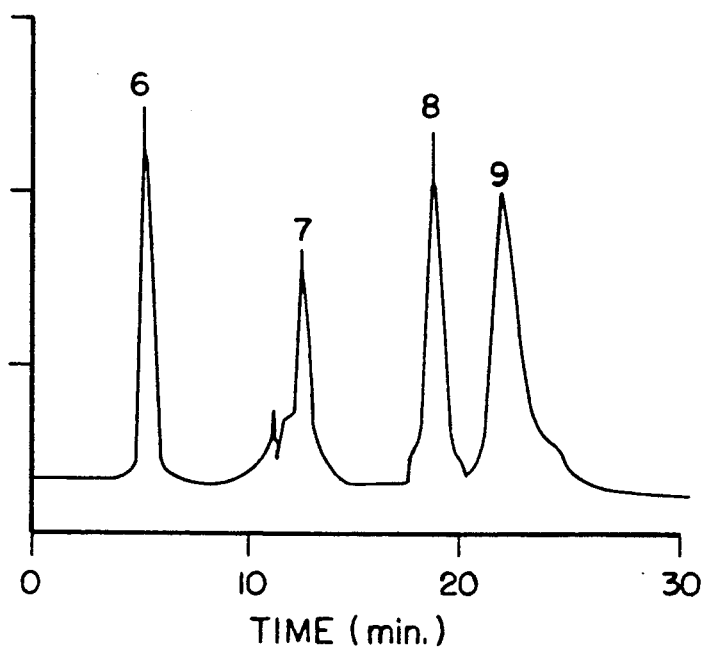

As was in Example 1, the carrier was evaluated. As for the pressure resistance, the pressure loss and the flow rate were in proportion to each other up to 80 kg/cm$^2$. In the swelling property test, the column pressure increased by 20 kg/cm$^2$ when the eluent was changed from a 40 mM phosphate buffer to a 200 mM phosphate buffer. Thus, it is apparent that the carrier particles obtained in this comparative example were inferior to the carrier particles of Example 1 in the pressure resistance and the swelling property. The ion exchanging ability measured by titration was 1.0 meq/g. The specific surface area was 80 m$^2$/g and the radius of the pore was 40 angstroms. When the carrier particles were treated with a silver nitrate solution to measure the thickness of the coated layer, it was found that carboxyl groups existed also in the carrier particles. Then, human blood was analyzed by Hi-AUTO $A_{1c}$ produced by Kyoto Daiichi Kagaku Kabushiki Kaisha. Since the retaining time is shortened in using eluent A, the elution condition was tested with diluted eluent A. As a result, it was found that the most adequate pattern was obtained in using the 1.67-fold diluted eluent A. The obtained chromatogram is shown in FIG. 5. Moreover, protein was separated by using the liquid chromatograph SSLC-20 produced by Sekisui Kagaku Kogyo Kabushiki Kaisha. The resultant chromatogram is shown in FIG. 6. Comparing FIGS. 5 and 6 with FIGS. 1 and 2, it is apparent that this carrier has a weaker retaining ability of protein and glycosylated hemoglobins and is inferior in separating ability. Especially, since HbF and unstable type of $HbA_{1c}$ can not be completely separated from stable type of $HbA_{1c}$, they can not be measured separately. Repeating the above measurements 3000 times decreased the separating ability, and the measured value of $HbA_{1c}$ was reduced to 70% of the initial value. In this way, when this carrier is repeatedly used, it is difficult to obtain an accurate measured value.

COMPARATIVE EXAMPLE 2

A hydrophobic crosslinked polymer was prepared in the same manner as in Example 1. Further, when a polymerization was performed with 300 g of acrylic acid as the monomer having a carboxyl group in the same manner as in Example 1, a coagulation occurred during the reaction, thereby obtaining 180 g of soft fine polymer particles. The polymer particles were classified in the same manner as in Example 1. The classified particles could not be packed in a column, since the particles were so soft that they stopped flowing while packing the column. The ion exchanging ability of the carrier particles measured by titration was 1.2 meq/g. The specific surface area was 0.6 $m^2/g$ an there were no pores. The thickness of the coated layer measured after treating the carrier particles with a silver nitrate solution was about 400 angstroms.

COMPARATIVE EXAMPLE 3

A hydrophobic crosslinked polymer was prepared in the same manner as in Example 1. Further, the same processes as Example 1 were repeated with 10 g of acrylic acid as the monomer having a carboxyl group to obtain 180 g of fine polymer particles. The particles were classified to obtain a carrier with a particle diameter of 6 to 9 $\mu$m. Then, this carrier was evaluated.

As a result, as for the pressure resistance, the pressure loss and the flow rate were in proportion to each other up to 150 $kg/cm^2$. In the swelling property test, the column pressure did not increase when the eluent was changed from a 40 mM phosphate buffer to a 200 mM phosphate buffer. The ion exchanging ability measured by titration was 0.005 meq/g. The specific surface area was 70 $m^2/g$ and the average radius of the pore was 60 angstroms. The thickness of the coated layer measured after treating the carrier with a silver nitrate solution in the above-mentioned manner was about 8 angstroms. It was observed that part of the surface was not coated.

Figure 7:
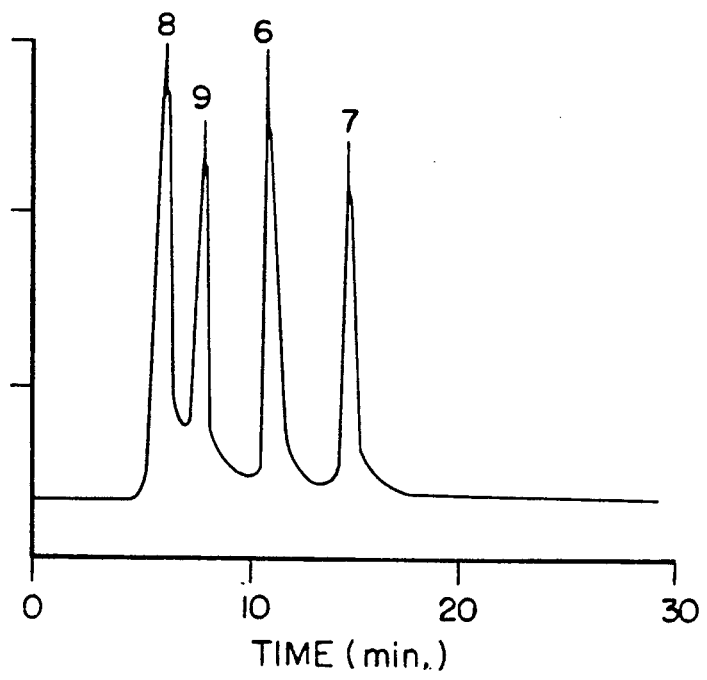

Moreover, protein was separated from a sample including several kinds of proteins by using the liquid chromatograph SSLC-20 produced by Sekisui Kagaku Kogyo Kabushiki Kaisha. The resultant chromatogram is shown in FIG. 7. It is regarded that the order of the elution was different from that of FIG. 2 since a hydrophobic interaction is caused between an uncoated portion and protein.

COMPARATIVE EXAMPLE 4

Four hundred fifty grams of triethyleneglycol dimethacrylate (a hydrophobic crosslinkable monomer), 50 g of tetramethylolmethane triacrylate (a hydrophobic crosslinkable monomer) and 1.5 g of benzoyl peroxide (a polymerization initiator) were uniformly mixed. The thus obtained mixture was added to 2.5 L of an aqueous solution of 4% polyvinyl alcohol and stirred to disperse an organic phase uniformly. After supplying nitrogen to displace the air in the reaction system, the mixture was heated to a temperature of 80° C. for a suspension polymerization for 8 hours. After the polymerization, the obtained product was successively washed with hot water and acetone, and dried to obtain a hydrophobic crosslinked polymer.

Three hundred grams of the obtained hydrophobic crosslinked polymer particles was immersed in 1 L of acetone with 0.5 g of benzoyl peroxide and 180 g of methacrylic acid dissolved therein, thereby impregnating with benzoyl peroxide and methacrylic acid. Then the acetone was removed under a reduced pressure at a temperature of 20° C. The above impregnated hydrophobic crosslinked polymer was suspended in 2 L of an aqueous solution of 20% sodium chloride including 5 g of polyvinyl alcohol, and allowed for a polymerization reaction at a temperature of 80° C. for 5 hours in an atmosphere of nitrogen. The obtained product was successively washed with hot water and acetone and dried to obtain 460 g of fine polymer particles. The particles were classified in the same manner as in Example 1, and those with a particle diameter of 6 to 9 $\mu$m were recovered to obtain a carrier. The carrier was evaluated in the same manner as in Example 1.

As for the pressure resistance, the pressure loss was in proportion to the flow rate up to 400 $kg/m^2$. In the swelling property test, the column pressure increased by 15 $kg/cm^2$, when the eluent was changed from a 40 mM phosphate buffer to a 200 mM phosphate buffer. Thus, it is obvious that the carrier obtained in this comparative example is inferior to the carrier of Example 4 in the pressure resistance and the swelling property. The ion exchanging ability measured by titration was 0.2 meq/g. The specific surface area was 0.5 $m^2/g$ and there were no pores.

Human blood was analyzed by Hi-AUTO $A_{1c}$ produced by Kyoto Daiichi Kagaku Kabushiki Kaisha. However, since this carrier had a weak retaining ability, an elution condition was tested with diluted eluent A. As a result, when a separation was performed with 2-fold diluted eluent A, the most adequate pattern was obtained. The obtained chromatogram was the same as FIG. 5. Comparing with FIG. 1, it is obvious that this carrier is inferior in separating ability. It was found from the chromatogram after measuring 3000 samples that the separating ability was further degraded and the measured value of $HbA_{1c}$ was decreased to 60% of the initial value.

Next, a separation was performed under the same condition as the above with a sample including several kinds of proteins by the liquid chromatograph system SSLC-20 produced by Sekisui Kagaku Kogyo Kabushiki Kaisha. The resultant chromatogram was the same as FIG. 6. Comparing with FIG. 2, it was found the carrier of this comparative example was clearly inferior in separating ability.

EXAMPLE 5

A hydrophobic crosslinked polymer was prepared in the same manner as in Example 1. Two hundred grams of the hydrophobic crosslinked polymer particles were immersed in 1 L of acetone with 0.5 g of acetyl peroxide (a polymerization initiator) dissolved therein to adhere the polymerization initiator. Next, the acetone was removed under a reduced pressure at a temperature of 20° C. The above immersed hydrophobic crosslinked polymer was dispersed in 2 L of an aqueous solution of 50% methanol, and 50 g of methyl acrylate (the monomer having a hydrolyzable group) was added thereto with stirring, and allowed for a polymerization reaction for 5 hours at a temperature of 70° C. in an atmosphere of nitrogen. The obtained product was successively washed with hot water and acetone and dried to obtain 180 g of fine polymer particles. A hundred fifty grams of the obtained fine polymer particles was added to 500 ml of a 20% by weight methanol solution of sodium hydroxide and heated at a temperature of 75° C. for 5 hours to hydrolyze an ester portion of the resin derived from methyl polyacrylate. After cooling down the reaction mixture to room temperature, the polymer particles were obtained by filtration, washed several times and dried. The thus obtained polymer particles were classified by the air classifier, Turbo Classifier TC-15N produced by Nisshin Engineering Kabushiki Kaisha, and those with a particle diameter of 8 to 10 μm were recovered to pack in a stainless column with an inner diameter of 6 mm and a length of 75 mm. Two grams of the carrier particles were added to 35 mL of a pure water, the resultant mixture was stirred for 5 minutes and the column was packed with it in a constant flow rate of 2.0 mL/minute.

The carrier was evaluated in the same manner as in Example 1. As for the pressure resistance, the pressure loss was in proportion to the flow rate up to 150 kg/cm$^2$. In the swelling property test, the column pressure did not increase when the eluent was changed from a 40 mM phosphate buffer to a 200 mM phosphate buffer. The ion exchanging ability measured by titration was 0.7 meq/g. The average thickness of the coated layer measured after treating the carrier with a silver nitrate solution in the above manner was about 100 angstroms. The specific surface area was 50 m$^2$/g and the average radius of the pore was 30 angstroms.

Figure 8:
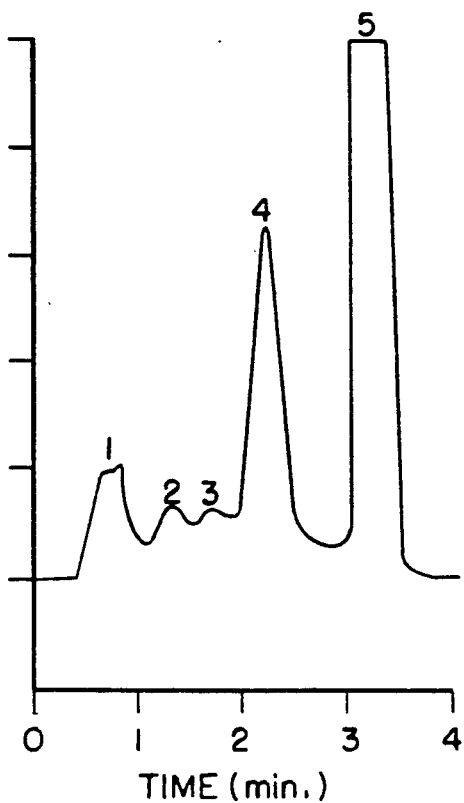
Figure 9:
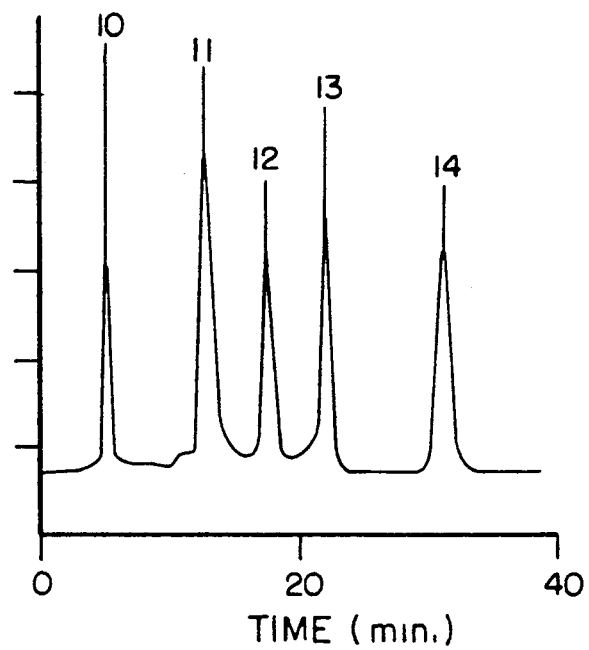
FIGS. 9, 11 and 13 to 15 show chromatograms obtained in separation of various proteins utilizing columns packed with carrier obtained in Example 5, Example 6 and Comparative Examples 5 to 7, respectively.

Human blood was analyzed by Hi-AUTO A$_{1c}$ produced by Kyoto Daiichi Kagaku Kabushiki Kaisha. The resultant chromatogram is shown in FIG. 8. The chromatogram and the measured value of HbA$_{1c}$ did not change after 3000 measurements were performed. Moreover, a sample containing several kinds of proteins was separated by using the liquid chromatograph system SSLC-20 produced by Sekisui Kagaku Kogyo Kabushiki Kaisha. The resultant chromatogram is shown in FIG. 9. In FIG. 9, and the following FIGS. 11 and 13, the peak with a reference numeral 10 results from myoglobin, 11 from trypsinogen, 12 from ribonuclease A, 13 from cytochrome C and 14 from lisozyme.

EXAMPLE 6

A hydrophobic crosslinked polymer was prepared in the same manner as in Example 1. Two hundred grams of the obtained hydrophobic crosslinked polymer particles was immersed in 1 L of acetone with 0.5 g of acetyl peroxide (a polymerization initiator) dissolved therein, thereby adhering the polymerization initiator. Next, the acetone was removed under a reduced pressure at a temperature of 20° C. The above immersed hydrophobic crosslinked polymer was suspended in 2 L of an aqueous solution of 50% methanol, and 50 g of acrylonitrile (the monomer having a hydrolyzable group) was added thereto with stirring and allowed for a polymerization reaction at a temperature of 70° C. for 10 hours in an atmosphere of nitrogen. The obtained product was successively washed with hot water and acetone and dried to obtain 180 g of fine polymer particles. These polymer particles were hydrolyzed in the same manner as in Example 5. The obtained polymer particles were classified to obtain a carrier with a particle diameter of 8 to 10 μm. This carrier was evaluated in the same manner as in Example 1.

Figure 10:
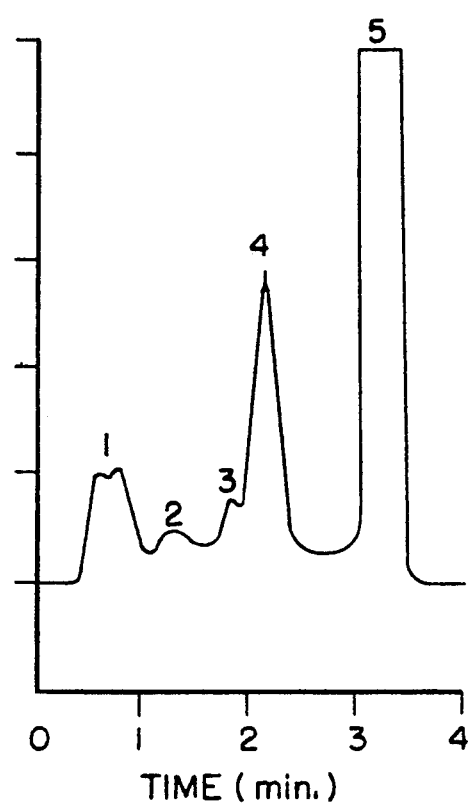
Figure 11:
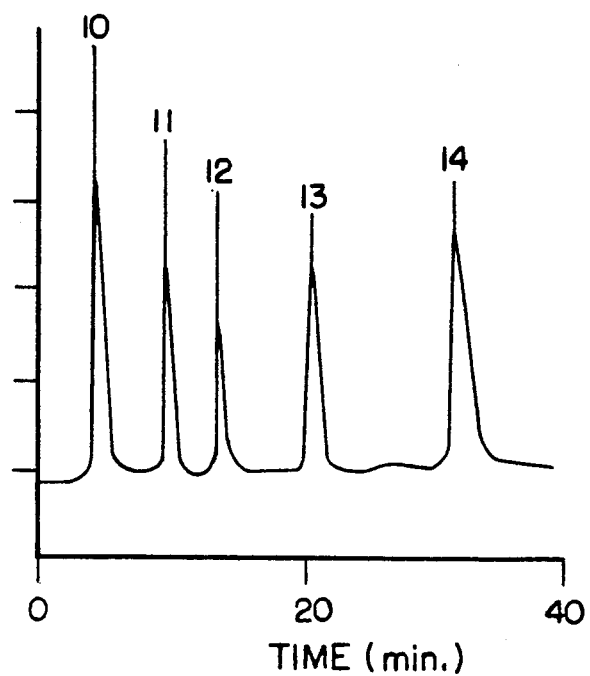

As a result, as for the pressure resistance, the pressure loss was in proportion to the flow rate up to 150 kg/cm$^2$. In the swelling property test, the column pressure did not increase when the eluent was changed from a 40 mM phosphate buffer to a 200 mM phosphate buffer. The ion exchanging ability of the carrier measured by titration was 0.8 meq/g. The average thickness of the coated layer after treating the carrier with a silver nitrate solution was about 70 angstroms. The specific surface area was 50 m$^2$/g, and the average radius of the pore was 30 angstroms. Human blood was separated in the same manner as in Example 1. The resultant chromatogram is shown in FIG. 10. The chromatogram and the measured value after repeating 3000 measurements were the same. Next, a sample including several kinds of proteins was separated in the same manner as in Example 5. The resultant chromatogram is shown in FIG. 11.

EXAMPLE 7

In this example, a continuous method in which the monomer having a hydrolyzable group is reacted subsequently after the preparation of hydrophobic crosslinked polymer particles was adopted.

A hundred grams of styrene, 200 g of divinylbenzene and 1 g of benzoyl peroxide were dissolved in 200 g of toluene. The resultant mixture was added to 2.5 L of an aqueous solution of 4% polyvinyl alcohol, stirred to disperse an organic phase uniformly, and heated to a temperature of 80° C. in an atmosphere of nitrogen for a suspension polymerization. After polymerizing for 2 hours, 50 g of acrylamide (the monomer having the hydrolyzable group) was added to the above system, and allowed to polymerize at a temperature of 80° C. for 2 hours. The obtained product was successively washed with hot water and acetone and dried to obtain 260 g of fine polymer particles. Two hundred grams of these polymer particles was added to 500 mL of a 20% by weight methanol solution of sodium hydroxide, and the mixture was heated at a temperature of 75° C. for 10 hours. The reaction mixture was cooled down to room temperature, washed several times with water and dried. The obtained polymer particles were classified in the same manner as in Example 1 in order to obtain a carrier with a particle diameter of 8 to 10 μm. The carrier was evaluated in the same manner as in Example 1.

As a result, as for the pressure resistance, the pressure loss and the flow rate were in proportion to each other up to 150 kg/cm$^2$. In the swelling property test, the column pressure did not increase when the eluent was changed from a 40 mM phosphate buffer to a 200 mM phosphate buffer. The ion exchanging ability measured by titration was 0.7 meq/g. The specific surface area was 60 m$^2$/g and the average radius of the pore was 40 angstroms. The average thickness of the coated layer measured after treating the carrier with a silver nitrate solution was about 80 angstroms. Human blood was analyzed in the same manner as in Example 1, and a sample containing various proteins was separated in the same manner as in Example 5. The resultant chromatograms were the same as FIGS. 8 and 9, respectively. The chromatogram and the measured value after 3000 analyses of human blood were the same.

EXAMPLE 8

Also in this example, a continuous method in which a monomer having a hydrolyzable group is reacted subsequently after the preparation of hydrophobic crosslinked polymer particles was adopted.

A hundred grams of styrene, 200 g of divinylbenzene and 1 g of benzoyl peroxide were dissolved in 200 g of toluene. The mixture was added to 2 L of an aqueous solution of 4% polyvinyl alcohol, stirred to disperse an organic phase uniformly, and heated to a temperature of 80° C. in an atmosphere of nitrogen for a suspension polymerization. After polymerizing for 4 hours, 50 g of 2-hydroxyethyl methacrylate (the monomer having the hydrolyzable group) was added thereto, and allowed to polymerize at a temperature of 80° C. for another 2 hours. The thus obtained product was successively washed with hot water and acetone and dried to obtain 260 g of fine polymer particles. The obtained polymer particles were hydrolyzed in the same manner as in Example 5 and classified to obtain a carrier with a particle diameter of 8 to 10 μm. The carrier was evaluated in the same manner as in Example 1.

As a result, as for the pressure resistance, the pressure loss and the flow rate were in proportion to each other up to 150 kg/cm$^2$. In the swelling property test, the column pressure did not increase when the eluent was changed from a 40 mM phosphate buffer to a 200 mM phosphate buffer. The ion exchanging ability measured by titration was 0.6 meq/g. The specific surface area was 60 m$^2$/g and the average radius of the pore was 40 angstroms. The average thickness of the coated layer measured after treating the carrier with a silver nitrate solution in the above manner was about 100 angstroms. Human blood was analyzed in the same manner as in Example 1, and a sample containing various proteins was separated in the same manner as in Example 5. The resultant chromatograms were the same as FIGS. 8 and 9, respectively. The chromatogram and the measured value after 3000 analyses of human blood were the same.

COMPARATIVE EXAMPLE 5

A hundred grams of styrene, 200 g of divinylbenzene, 70 g of methyl acrylate (the monomer having a hydrolyzable group) and 1 g of acetyl peroxide were dissolved in 200 g of toluene. The mixture was added to 2.5 L of an aqueous solution of 4% polyvinyl alcohol, stirred to disperse an organic phase uniformly and heated to 70° C. for a suspension polymerization. After polymerizing for 8 hours, 340 g of fine polymer particles was obtained. The thus obtained product was hydrolyzed in the same manner as in Example 5. The hydrolyzed product was classified in the same manner as in Example 1 to obtain carrier particles with a particle diameter of 6 to 9 μm. This carrier was evaluated in the same manner as in Example 1.

Figure 12:
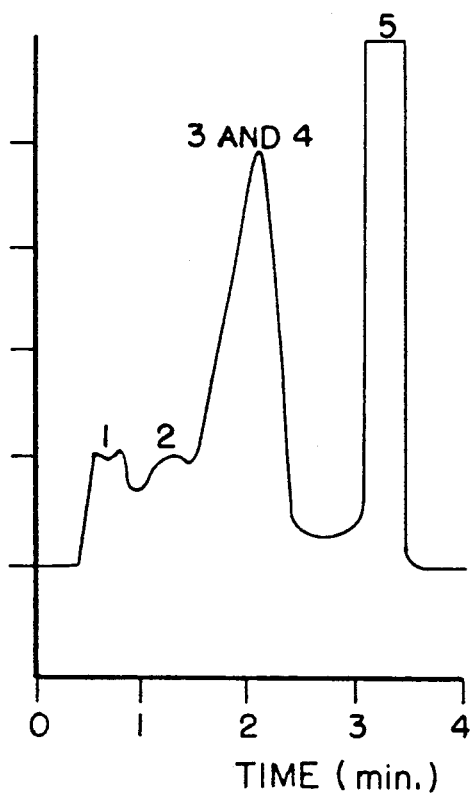
Figure 13:
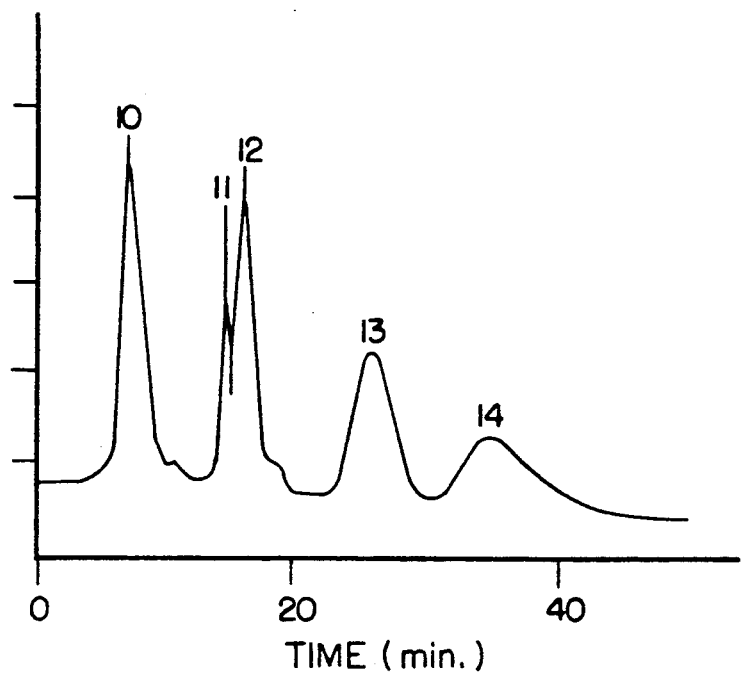

As for the pressure resistance, the pressure loss was in proportion to the flow rate up to 80 kg/cm$^2$. In the swelling property test, the column pressure increased by 20 kg/cm$^2$ when the eluent was changed from a 40 mM phosphate buffer to a 200 mM phosphate buffer. Thus, it is apparent that the carrier of this comparative example is inferior to the carrier of Example 5 in the pressure resistance and the swelling property. The ion exchanging ability measured by titration was 1.0 meq/g. The specific surface area was 60 m$^2$/g and the average radius of the pore was 30 angstroms. When the carrier was treated with a silver nitrate solution to measure the average thickness of the coated layer, it was found that carboxyl groups existed uniformly in the carrier particles. Moreover, human blood was analyzed in the same manner as in Example 1. The result is shown in FIG. 12. Since this carrier had a weak retaining ability, the elution condition was tested with diluted eluent A. As a result, the most adequate pattern was obtained when the 1.43-fold diluted eluent A was used. Comparing FIG. 12 with FIG. 8, this carrier was found to be clearly inferior in separating ability. It was found from the chromatogram after repeating 3000 analyses of human blood that the separating ability was further degraded and that the measured value of HbA$_{1c}$ was decreased to 60% of the initial value. Next, a sample containing several kinds of proteins was separated in the same manner as in Example 5. The result is shown in FIG. 13. Comparing FIG. 13 with FIG. 9, it is apparent that this carrier is inferior in separating ability.

COMPARATIVE EXAMPLE 6

Hydrophobic crosslinked polymer particles were prepared in the same manner as in Example 1. A polymerization in the same process as in Example 5 was performed with 300 g of methyl acrylate as the monomer having a hydrolyzable group to coat the hydrophobic crosslinked polymer particles, thereby obtaining 180 g of fine polymer particles. The obtained product was hydrolyzed in the same manner as in Example 5. The particles were classified in the same manner as in Example 1 in order to obtain carrier particles with a particle diameter of 6 to 9 μm. This carrier was evaluated in the same manner as in Example 1.

As a result, as for the pressure resistance, the pressure loss and the flow rate were in proportion to each other up to 150 kg/cm$^2$. In the swelling property test, the column pressure increased by 25 kg/cm$^2$ when the eluent was changed from a 40 mM phosphate buffer to a 200 mM phosphate buffer. This seems to be because the carrier particles of this comparative example are inferior in the swelling property since the coated layer having the carboxyl groups is thick. The ion exchanging ability of the carrier measured by titration was 1.2 meq/g. The average thickness of the coated layer measured after treating the carrier particles with a silver nitrate solution was about 400 angstroms. The specific surface area was 1.5 m$^2$/g. The coated layer was thick and there were few pores.

A sample containing several kinds of proteins were separated in the same manner as in Example 5. The resultant chromatogram is shown in FIG. 14.

Figure 14:
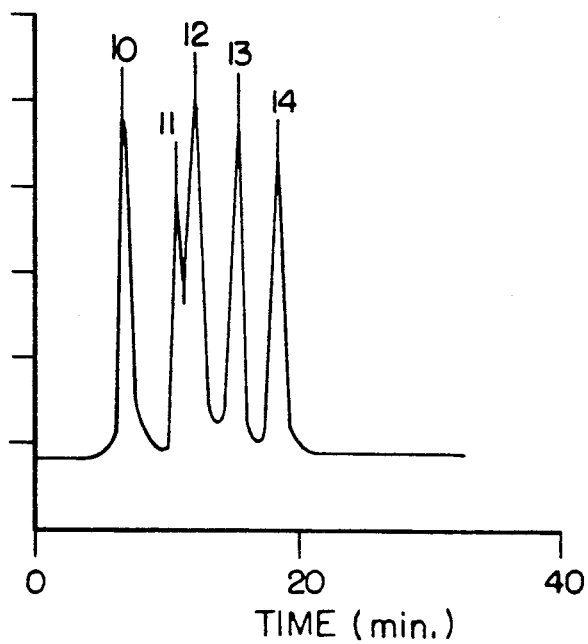

FIG. 14 shows that the carrier of this comparative example has a weaker retaining ability than the carriers of Examples 5 and 6 (shown in FIGS. 9 and 11). This seems to be because there are few pores as mentioned above and the surface area is small.

COMPARATIVE EXAMPLE 7

Hydrophobic crosslinked polymer particles were prepared in the same manner as in Example 1. A polymerization in the same process as in Example 5 using 10 g of methyl acrylate as the monomer having a hydrolyzable group was performed to coat the hydrophobic crosslinked polymer particles, thereby obtaining 180 g of fine polymer particles. The obtained product was hydrolyzed in the same manner as in Example 5. The particles were classified in the same manner as in Example 1 to obtain carrier particles of a particle diameter of 6 to 9 μm. This carrier was evaluated in the same manner as in Example 1.

As a result, as for the pressure resistance, the pressure loss and the flow rate were in proportion to each other up to 150 kg/cm$^2$. In the swelling property test, the column pressure did not increase when the eluent was changed from a 40 mM phosphate buffer to a 200 mM phosphate buffer. The ion exchanging ability of the carrier particles measured by titration was 0.1 meq/g. The specific surface area was 70 m$^2$/g and the average radius of the pores was 60 angstroms. The average thickness of the coated layer measured after treating the carrier particles with a silver nitrate solution was about 8 angstroms. Part of the surface of the carrier particles was not coated.

Figure 15:
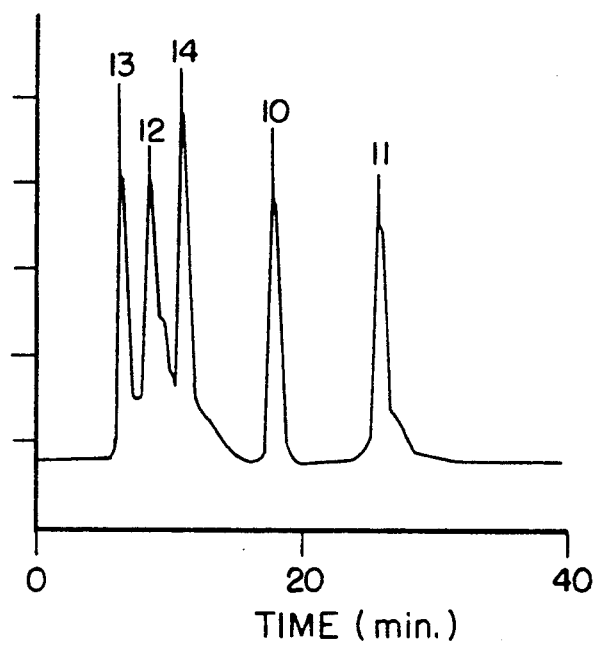

A sample containing several kinds of proteins was separated in the same manner as in Example 5. The resultant chromatogram is shown in FIG. 15. In the chromatogram of FIG. 15, the eluting order is different from that of FIGS. 9 and 11. This seems to be because the hydrophobic interaction is caused due to the insufficient coating of the hydrophobic crosslinked polymer particles.

INDUSTRIAL APPLICABILITY

As described above, the present invention provides a carrier for cation exchange liquid chromatography which as a satisfactory pressure resistance, hardly swells or shrinks and does not absorb protein nonspecifically. Such a carrier can be utilized in a wide range for isolating or analyzing various kinds of hydrophilic materials. Such a carrier is especially effective for determining glycosylated hemoglobins. The glycosylated hemoglobins can be determined accurately in a short period of time. By determining the glycosylated hemoglobins in blood, diabetes and the like can be diagnosed rapidly and accurately.

We claim:

1. A production method of a carrier for cation exchange liquid chromatography comprising the steps of:
   providing an aqueous dispersion in which hydrophobic crosslinked polymer particles to which a polymerization initiator is adhered are dispersed; and
   adding a polymerizable monomer having a carboxyl group to the aqueous dispersion and polymerizing the monomer on the surface of the hydrophobic crosslinked polymer particle, thereby forming a polymer layer having carboxyl groups on the surface of the hydrophobic crosslinked polymer particle to obtain a coated polymer particle,
   wherein said hydrophobic crosslinked polymer is obtained by homopolymerizing or copolymerizing at least one kind of a hydrophobic crosslinkable monomer, or copolymerizing at least one kind of a hydrophobic crosslinkable monomer and at least one kind of a hydrophobic noncrosslinkable monomer, where said hydrophobic crosslinkable monomer is selected from the group consisting of poly(meth)acrylates and aromatic compounds having at least two vinyl groups;
   and further wherein said polymerizable monomer having a carboxyl group selected from the group consisting of acrylic acid, methacrylic acid, maleic acid, fumaric acid and crotonic acid.

2. A production method according to claim 1, wherein the hydrophobic noncrosslinkable monomer is at least one selected from the group consisting of (meth)acrylates, vinyl acetate and styrene monomers.

3. A production method according to claim 1, wherein the hydrophobic crosslinkable monomer for preparing the hydrophobic crosslinked polymer is used at a rate of 10 parts by weight or more for every 100 parts by weight of the entire monomers.

4. A production method according to claim 1, wherein the polymerizable monomer having a carboxyl group is added at a rate of 5 to 80 parts by weight for every 100 parts by weight of the hydrophobic crosslinked polymer particles.

5. A production method according to claim 1, wherein the polymerization initiator is at least one selected from the group consisting of organic peroxides and azo compounds.

6. A production method according to claim 1, wherein the temperature of the aqueous dispersion at the time of the polymerization is 40° to 100° C. and reaction time thereof is 0.5 to 40 hours.

7. A production method according to claim 1, wherein the average particle diameter of the coated polymer particle is 1 to 1000 μm.

8. A production method according to claim 1, wherein the coated polymer particle substantially does not have any pores or is a porous particle with pores having an average radius of 10,000 angstroms or less.

9. A production method according to claim 1, wherein the aqueous dispersion in which the hydrophobic crosslinked polymer to which the polymerization initiator is adhered is dispersed is obtained by reacting monomers including a hydrophobic crosslinkable monomer in the presence of the polymerization initiator.

10. A production method of a carrier for a cation exchange liquid chromatography comprising the steps of:
    providing an aqueous dispersion in which hydrophobic crosslinked polymer particles without any hydrolyzable groups to which a polymerization initiator is adhered are dispersed;
    adding a ethylenically unsaturated monomer having a functional group which can be converted into a carboxyl group by a hydrolytic reaction to the aqueous dispersion to be dissolved therein and polymerizing the monomer on the surface of the polymer particle, thereby forming a layer of the polymer having the functional groups on the surface of the hydrophobic crosslinked polymer particle; and
    hydrolyzing the functional groups to obtain a coated polymer particle having carboxyl groups on the surface thereof,
    wherein said hydrophobic crosslinked polymer is obtained by homopolymerizing or copolymerizing at least one kind of a hydrophobic crosslinkable monomer, or copolymerizing at least one kind of a hydrophobic crosslinkable monomer and at least one kind of a hydrophobic noncrosslinkable monomer, where said hydrophobic crosslinkable monomer is an aromatic compound having at least two vinyl groups.

11. A production method according to claim 10, wherein the hydrophobic noncrosslinkable monomer is a styrene monomer.

12. A production method according to claim 10, wherein the hydrophobic crosslinkable monomer for preparing the hydrophobic crosslinked polymer is used at a rate of 10 parts by weight or more for every 100 parts by weight of the entire monomers.

13. A production method according to claim 10, wherein the monomer having the functional group which can be converted into a carboxyl group by a hydrolytic reaction is selected from the group consisting of alkyl (meth)acrylates, (meth)acrylamide and (meth)acrylonitrile.

14. A production method according to claim 10, wherein the monomer having the functional group which can be converted into a carboxyl group by a hydrolytic reaction is added at a rate of 5 to 80 parts by weight for every 100 parts by weight of the hydrophobic crosslinked polymer particles.

15. A production method according to claim 10, wherein temperature of the aqueous dispersion at the time of the polymerization is 40° to 100° C. and reaction time is 0.5 to 40 hours.

16. A production method according to claim 10, wherein the hydrolytic reaction is performed by treating the hydrophobic crosslinked polymer particle with the polymer layer having the functional groups which can be converted into a carboxyl group by a hydrolytic reaction formed thereon in an acidic or an alkaline solution.

17. A production method according to claim 10, wherein the average particle diameter of the coated polymer particle is 1 to 1000 μm.

18. A production method according to claim 10, wherein the coated polymer particle does not substantially have any pores or is a porous particle with pores having an average radius of 10,000 angstroms or less.

19. A production method according to claim 10, wherein the aqueous dispersion in which the hydrophobic crosslinked polymer to which the polymerization initiator is adhered is dispersed is obtained by reacting monomers including the hydrophobic crosslinkable monomer without a hydrolyzable group in the presence of the polymerization initiator.

* * * * *